United States Patent [19]

Duffy

[11] 4,125,725
[45] Nov. 14, 1978

[54] PHENYLATED CARBOXYQUINOXALINES

[75] Inventor: James V. Duffy, Beltsville, Md.

[73] Assignee: The United States of America as represented by the Secretary of the Navy, Washington, D.C.

[21] Appl. No.: 803,333

[22] Filed: Jun. 3, 1977

Related U.S. Application Data

[63] Continuation-in-part of Ser. No. 674,254, Apr. 6, 1976, abandoned.

[51] Int. Cl.² ............................................. C07d 241/42
[52] U.S. Cl. .................................. 544/353; 528/332; 528/310; 528/327
[58] Field of Search ....................... 260/250 Q; 544/353

[56] References Cited

U.S. PATENT DOCUMENTS

| | | | |
|---|---|---|---|
| 3,656,953 | 4/1972 | Schluwke et al. | 96/20 |
| 4,001,017 | 1/1977 | Baumann et al. | 96/35.1 |

FOREIGN PATENT DOCUMENTS 2,010,280  9/1970  Fed. Rep. of Germany.

OTHER PUBLICATIONS

Chemical Abstracts, 56, 5957 b, (1960) Musante et al.

Primary Examiner—Nicholas S. Rizzo
Assistant Examiner—Mark L. Berch
Attorney, Agent, or Firm—R. S. Sciascia; A. L. Branning; R. D. Johnson

[57] ABSTRACT

High molecular weight polyphenylamide-quinoxalines comprised essentially of units of the formula

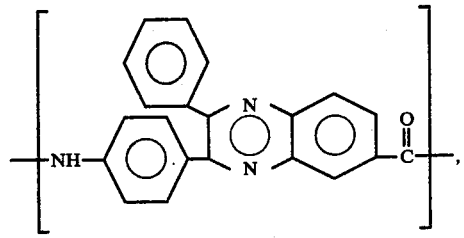

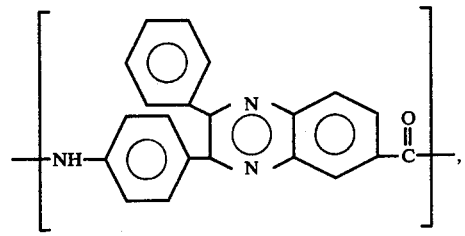

or mixtures thereof, are prepared by heating bifunctional monomers of the formula

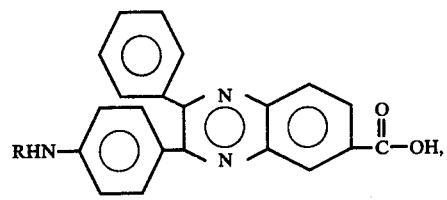

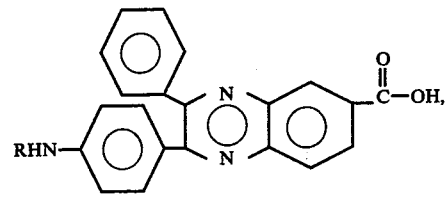

or mixtures thereof, wherein R is $COCH_3$ or —H to a temperature above the melting point of the monomer but below the decomposition temperature of the polyphenylamide-quinoxaline (Ca. 475–490° C). This melt polymerization of the bifunctional monomers produces strong, low void adhesive joints.

13 Claims, No Drawings

PHENYLATED CARBOXYQUINOXALINES

CROSS-REFERENCE TO RELATED APPLICATION

The present application is a continuation-in-part of copending application, Ser. No. 674,254, filed on Apr. 6, 1976, entitled "Meltable Bifunctional Quinoxaline Monomer and Preparation of a Polymer Therefrom", now abandoned.

BACKGROUND OF THE INVENTION

This invention relates generally to polymers and more particularly to polyphenylamide-quinoxalines.

Polyphenylquinoxalines have been described in application Ser. No. 876,572, filed Nov. 13, 1969, entitled, "Phenylated Polyquinoxalines and Method of Preparation Thereof" by Wolfgang J. Wrasidlo, now abandoned. Furthermore, phenylated imide-quinoxaline copolymers are also known and have been disclosed in U.S. Pat. No. 3,642,700 entitled "Phenylated Imide-Quinoxaline Copolymers and Method of Their Preparation" issued to Joseph M. Augl. Additionally, U.S. Pat. No. 3,654,226, entitled "Soluble Imide-Quinoxaline Copolymers" issued to Joseph M. Augl and James V. Duffy and U.S. Pat. No. 3,766,141 entitled "Polyquinoxalines Containing Flexibilizing Groups in the Polymer Chain" issued to Joseph M. Augl and Wolfgang Wrasidlo also disclosed similar types of polymers. As shown by data presented by J. M. Augl and W. Wrasidlo in "Phenylated Polyquinoxalines from 1,4-Bis(-phenylglyoxaloyl)benzene," Polymer letters, pp. 281–86 (1969), the polyphenylquinoxalines have better oxidative thermal stabilities than their corresponding unphenylated polyquinoxalines. Additionally, some of these polymers, even those with a relatively high molecular weight, are very soluble in common organic solvents; thus, coatings of these polymers may be conveniently removed from delicate components.

These prior art polyphenylquinoxaline polymers are formed by reacting an aromatic tetraamine, for example,

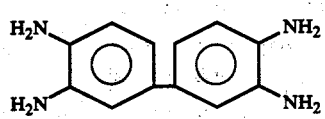

with a bis-benzil such as 1,4-bis-benzil,

As disclosed in the above-named patents, a number of aromatic tetramines may be reacted with any of a number of bis-benzils to produce the polyphenylquinoxalines. However, each of those prior art syntheses requires a two component monomer system, and this results in a number of problems and disadvantages. First, if high molecular weight polymers are to be produced, the monomer components must be very pure, accurately weighed, and carefully mixed together. Second, melt polymerization processes are impractical when two or more components having different melting points are required; in this regard, the tetraamines used frequently have high melting points. Third, these two component monomer systems require a solvent in order to insure the homogeneity and stoichiometry of the components and to promote the polymerization reactions. The solvent must be capable of dissolving the monomer components as well as the product polyphenylquinoxaline. Another problem with these prior art processes is that they require residual solvents to insure plasticization and good flow during processing. Removal of these solvents creates voids in the polyphenylquinoxaline polymers, and these voids reduce the strength and thermal stability of the polymers.

SUMMARY OF THE INVENTION

Accordingly, one object of this invention is to provide novel bifunctional quinoxaline monomers.

Another object of this invention is to provide bifunctional quinoxalines which polymerize upon melting to form polyphenylamidequinoxalines.

A further object of this invention is to provide bifunctional monomers which inherently contain the stoichiometry required for the attainment of high molecular weight polymers.

Still another object of this invention is to provide a solventless process for synthesizing high molecular weight polyphenylamide-quinoxalines.

A still further object of this invention is to provide solvent free prepregs and adhesive joints.

Yet another object of this invention is to provide prepregs and adhesive joints having low void contents.

Yet a further object of this invention is to provide polymers having high strengthes and good thermal stabilities.

Another object of this invention is to provide improved wetting of fibers and metal surfaces by polymers in prepregs and adhesive joints.

These and other objects of this invention are accomplished by providing a bifunctional quinoxaline monomer selected from the group consisting of

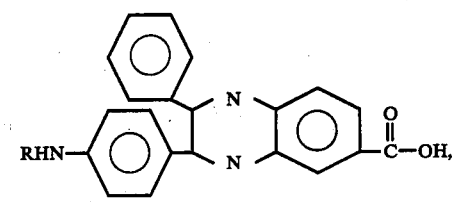

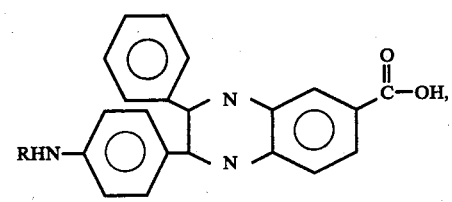

and mixtures thereof, wherein R is selected from the group consisting of

which polymerizes to form a high molecular weight polyphenylamide-quinoxaline which are comprised essentially of units selected from the group consisting of

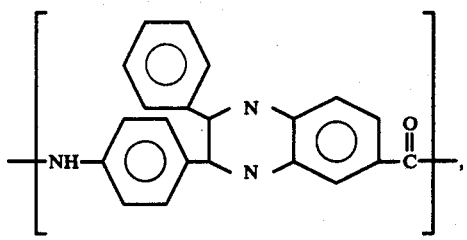

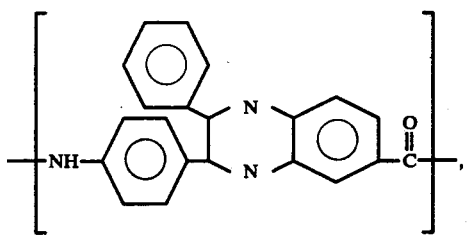

and mixtures thereof, respectively, when heated to a temperature above the melting points of the bifunctional monomers but below the decomposition temperature of the polyphenylamide-quinoxaline (Ca 475° C.) in an inert environment, such as a stream of nitrogen gas.

A mixture of the bifunctional acetamido-acid monomers

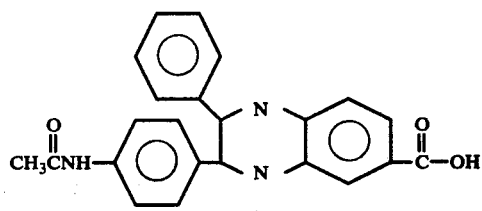

and

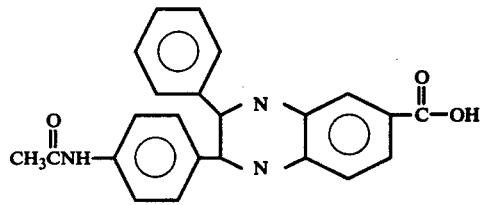

is formed by reacting 4-acetamidobenzil,

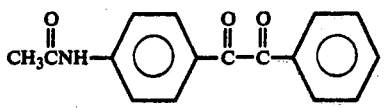

with 3,4-diaminobenzoic acid,

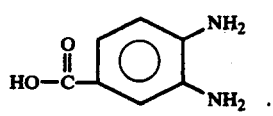

A mixture of amine-acid monomers

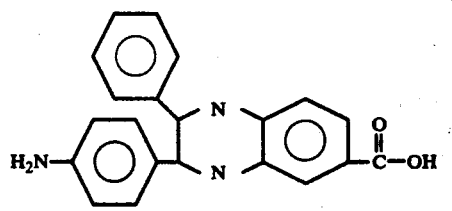

and

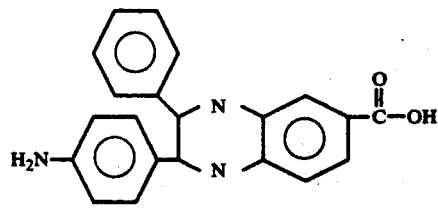

is produced by hydrolyzing the mixture of acetamido-acid monomers with a strong acid such as concentrated hydrochloric or a 1:1 (by volume) mixture of water and concentrated hydrochloric acid. Separation of either the acetamide-acid of the amine-acid monomer isomers may be accomplished by state of the art gas chromatography or liquid column chromatography procedures.

DESCRIPTION OF THE PREFERRED EMBODIMENT

The reaction sequence of the present invention can be summarized as follows:

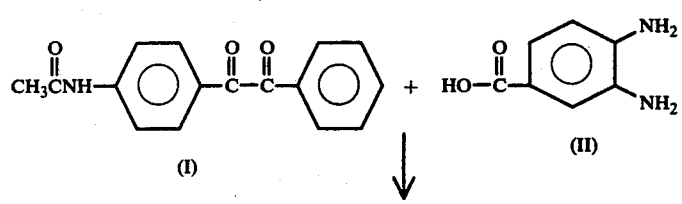

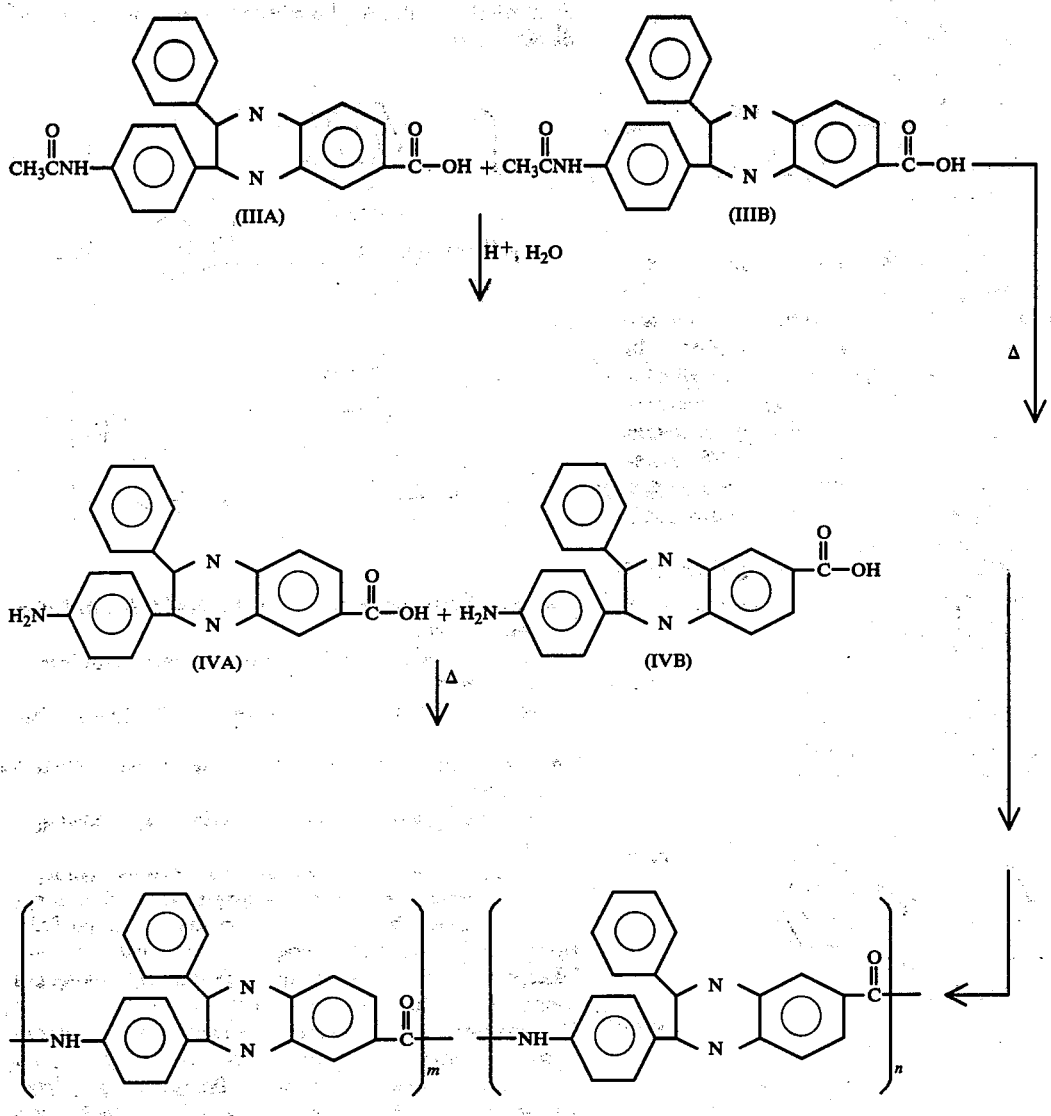

wherein, *m* and *n* are positive integers.

The acetamido-acid mixture of 3-(p-acetamidophenyl)-2-phenyl-6-carboxyquinoxaline [see formula IIIA] and 3-(p-acetamidophenyl)-2-phenyl-7-carboxyquinoxaline [see formula IIIB] is prepared by reacting 4-acetamidobenzil with 3,4-diaminobenzoic acid. A molecule of 4-acetamidobenzil can react with a molecule of 3,4-diaminobenzoic acid in either of two ways:

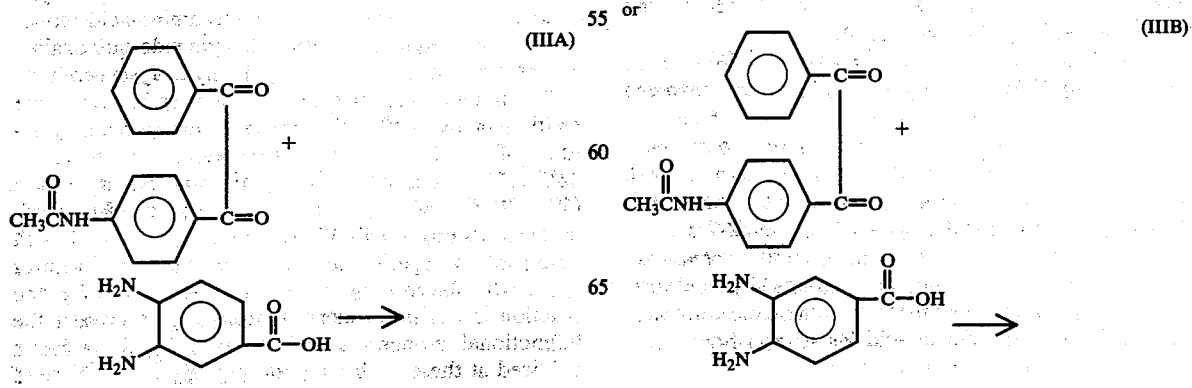

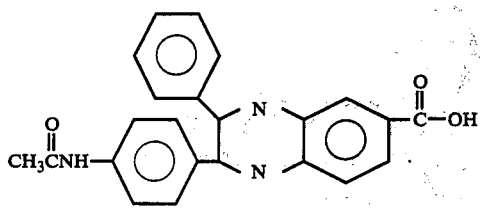

Thus, when an ordinary acid catalyst is used, a mixture of these isomers [IIIA and IIIB] will be produced. The reaction is run in a suitable solvent, such as meta-cresol, in which the reactants and products are soluble. It is also desirable that the solvent have a high enough boiling point that the reaction can be run at temperatures above 100° C. so that water formed during the reaction is driven off as vapor. Meta-cresol is the preferred solvent because, in addition to its high boiling point (202° C.) and ability to dissolve the reactants and products, it is an acid which catalyzes the reaction.

3,4-diaminobenzoic acid (II) is commercially available whereas 4-acetamidobenzil (I) can be prepared by the following reaction sequence:

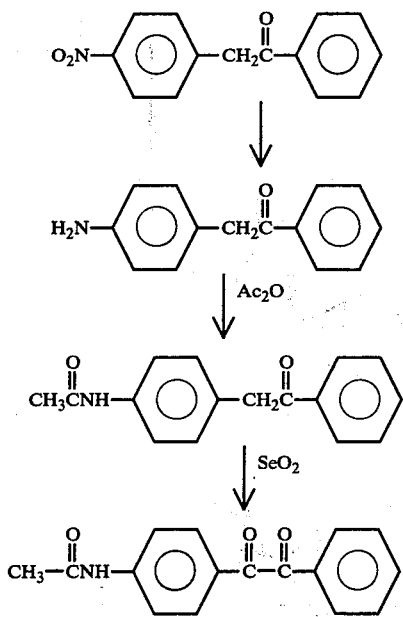

The details of the 4-acetamidobenzil preparation are disclosed in examples 1, 2, and 3 of both U.S. Pat. Nos. 3,642,700 and 3,654,226, hereinbefore referred to and hereby incorporated by reference.

The bifunctional amine-acid mixture of 3-(p-aminophenyl)-2-phenyl-6-carboxyquinoxaline [see formula IVA] and 3-(p-aminophenyl)-2-phenyl-6-carboxyquinoxaline [see formula IVB] is prepared by ordinary hydrolysis of the bifunctional acetamino-acid mixture of 3-(p-acetamidophenyl)-2-phenyl-6-carboxyquinoxaline [IIIA] and 3-(p-acetamidophenyl)-2-phenyl-7-carboxyquinoxaline [IIIB]. For instance, when the acetamino-acid mixture is refluxed with concentrated hydrochloric acid or a mixture of equal parts by volume of water and concentrated hydrochloric acid for several hours, the amino-acid mixture is produced.

The polyphenylamide-quinoxaline polymer which is comprised essentially of a mixture of repeating units of the formulas

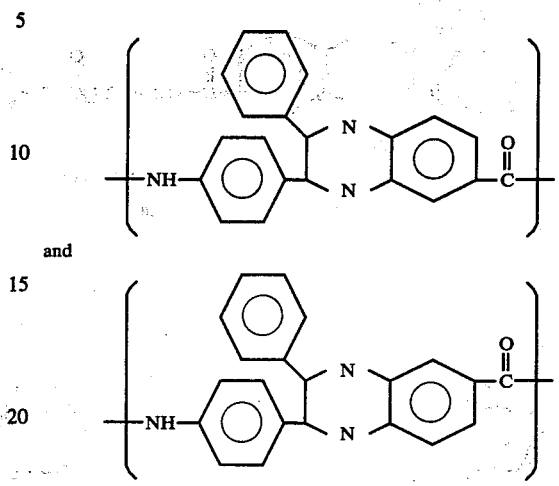

and is prepared by heating a mixture of the bifunctional acetamidoacid monomers, 3-(p-acetamidophenyl)-2-phenyl-6-carboxyquinoxaline and
3-(p-acetamidophenyl)-2-phenyl-7-carboxyquinoxaline, or by heating a mixture of the bifunctional amino-acid monomers 3-(p-aminophenyl)-2-phenyl-6-carboxyquinoxaline and
3-(p-aminophenyl)-2-phenyl-7-carboxyquinoxaline to a temperature above the melting point of the monomer but below the decomposition temperature of the polyphenylamide-quinoxaline in an inert environment. The polymerization of the bifunctional acetamido-acid monomer mixture produces acetic acid (vapor) as a by-product, whereas the polymerization of the bifunctional amino-acid monomer mixture produces water vapor as a by-product. If a strong, flexible high molecular weight polyphenylamide-quinoxaline is to be produced, the bifunctional monomer mixtures must be very pure. For instance, decomposition products, solvents, acids, or other contaminents should be carefully removed from the bifunctional monomer mixtures before the polymerization is attempted. However, the bifunctional acetamido-acid and amino-acid monomers do not interfere with each other in the polymerization process; therefore, a mixture of the bifunctional acetamido-acid monomer mixture and the bifunctional amino-acid monomer mixture may be used. Thus, even if the hydrolysis of the acetamido-acid monomers to amino-acid monomers is incomplete, the polyphenylamide-quinoxaline will still be formed by heating the hydrolysis product.

The polymerization temperature must be above the melting point of the bifunctional acetamido-acid mixture (M.P. 264°–6° C.) or amino-acid mixture (M.P. 225°–57° C.) but below the decomposition temperature. (475°–90° C.) of the polyphenylamide-quinoxaline product. For example, 350° C. has been found to work well in laboratory experiments; however, other temperatures within the above range may also be used. Finally, the reaction is run in an inert environment to protect the bifunctional monomers and the polymer from being oxidized at these high temperatures. An atmosphere of an inert gas such as nitrogen, helium, argon, etc. works well; and a stream of gas offers the advantage of removing the acetic acid or water vapor produced in the polymerization reaction.

Separation of the acetamide-acid isomeric mixture into pure 3-(p-acetamidophenyl)-2-phenyl-6-carboxyquinoxaline and pure 3-(p-acetamidophenyl)-2-phenyl-7-carboxyquinoxaline may be accomplished by state of the art gas chromatography or liquid column chromatography techniques. Moreover, by using these techniques, the amino-acid isomeric mixture may be separated into pure 3-(p-aminophenyl)-2-phenyl-6-carboxyquinoxaline and pure 3-(p-aminophenyl)-2-phenyl-7-carboxyquinoxaline. High molecular weight polyphenylamide-quinoxalines consisting essentially of units of the formula

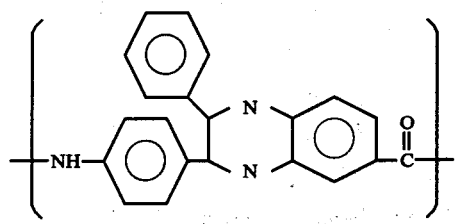

may be prepared from either 3-(p-acetamidophenyl)-2-phenyl-6-carboxyquinoxaline or 3-(p-aminophenyl)-2-phenyl-6-carboxyquinoxaline using the melt polymerization procedure described above. Similarly, polyphenylamide-quinoxalines consisting essentially of units of the formula

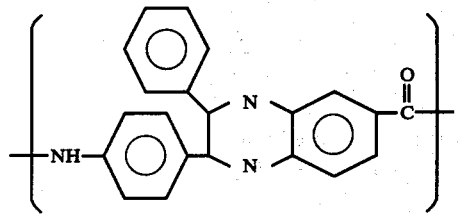

may be prepared from either 3-(p-acetamidophenyl)-2-phenyl-7-carboxyquinoxaline or 3-(p-aminophenyl)-2-phenyl-7-carboxyquinoxaline using the melt polymerization procedure described above. Admittedly, separation of the bifunctional isomers by gas chromatography or liquid column chromatography will be too slow and expensive for use in commercial processes. Nevertheless, samples of these pure isomers and their corresponding polymers may be prepared in the laboratory by these methods.

Strong, solvent-free prepregs and adhesive joints can be prepared by placing the fibers (e.g. graphite fibers) and metal surfaces in the bifunctional monomer melts during melt polymerization of the monomers. This procedure provides improved wetting of fibers in composites and of metal surfaces in adhesive joints by the polymers, resulting in stronger and more durable structures.

The general nature of the invention having been set forth, the following examples are presented as specific illustrations thereof. It will be understood that the invention is not limited to these specific examples but is susceptible to various modifications that will be recognized by one of the ordinary skill in the art.

EXAMPLE 1

Preparation of a mixture of 3-(p-acetamidophenyl)-2-phenyl-6-carboxyquinoxaline

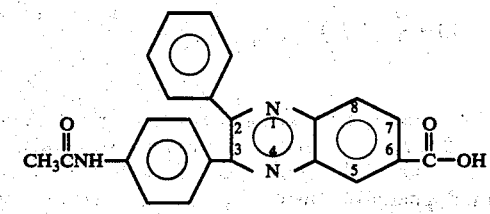

3-(p-acetamidophenyl)-2-phenyl-7-carboxyquinoxaline

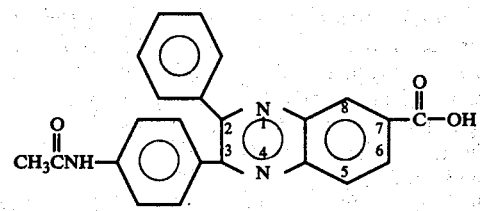

13.367 grams (0.05 moles) of 4-acetamidobenzil and 7.614 grams (0.05 moles) of 3,4-diaminobenzoic acid were added to 80 ml. of distilled meta-cresol and stirred overnight at room temperature. The solution turned red by morning and only a small amount of 3,4-diaminobenzoic acid remained undissolved. The solution was then heated at 100° C. for 2 hours. Next, petroleum ether (the 60°–110° C. fraction, i.e. Ligroin) and a small amount of acetone were added to the cresol solution until the product precipitated as a yellow solid. The yellow solid was soluble in acetone and ethyl alcohol but insoluble in toluene and chloroform. Recrystallization of the yellow solid precipitate was attempted in dioxane. The dioxane solidified overnight in an icebox. On warming to 15° C., the dioxane melted, but the precipitate remained a solid. The precipitate was then filtered and vacuum dried. M.P. 263°–266° C.

Analysis — Calcd for $C_{23}H_{17}N_3O_3$ (percent): C, 72.05; H, 4.47; N, 10.96; Found (percent): C, 71.90; H, 4.42; N, 10.81.

EXAMPLE 2

Preparation of a mixture of 3-(p-aminophenyl)-2-phenyl-6-carboxyquinoxaline

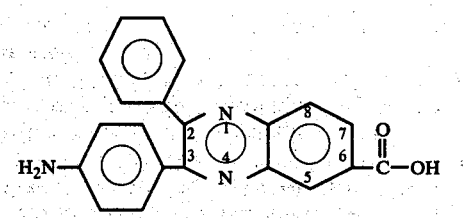

and 3-(p-aminophenyl)-2-phenyl-7-carboxyquinoxaline

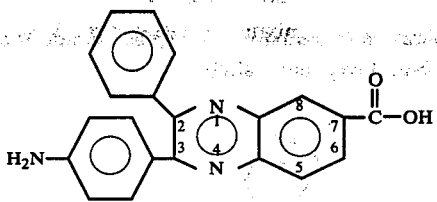

RUN I (using 1:1 water-concentrated hydrochloric acid) 3.0 grams of the mixture of 3-(p-acetamidophenyl)-2-phenyl-6-carboxyquinoxaline and 3-(p-acetamidophenyl)-2-phenyl-7-carboxyquinoxaline produced in Example 1 was heated in a mixture of 20 ml. of water and 20 ml. of concentrated hydrochloric acid at reflux temperature for 3 hours. The solid was collected on a Teflon filter, neutralized, and then converted to the water-soluble sodium salts; during this conversion the soldium salts were dissolved in the water forming a solution having a Ph of 10. The Ph was adjusted to between 7–8 at which time a precipitate formed. The precipitate was collected on a filter, washed with water, and vacuum dried. M.P. 256–258° C. with decomposition and gassing.

The Ph of the filtrate was adjusted to 4–5 and a great deal more solid precipitated and was collected on a filter. The filtrate from this was cloudy; however, when the Ph was adjusted to 2, the filtrate cleared up. Part of the solid formed at Ph 4–5 was recrystallized from tetrahydrofuran followed by washing in boiling toluene. M.P. 262–265. A second batch of the solid was recrystallized from a isopropyl alcohol-toluene mixture. M.P. 260–264° C. A mixed melting point determination indicates that the solid is the unhydrolyzed acetamido-acid mixture (M.P. 263–266° C.).

RUN II (using concentrated hydrochloric acid).

1.0 grams of the mixture of 3-(p-acetamidophenyl)-2-phenyl-6-carboxylquinoxaline and 3-(p-acetamidophenyl)-2-phenyl-7-carboxyquinoxaline produced in Example 1 was added to 100 ml of concentrated hydrochloric acid at room temperature. This mixture was dark red and not all of the solid dissolved. Upon heating the solid completely dissolves into the acid. The mixture was refluxed until a brownish solid precipitate was formed. The solution was made basic and solid dissolved again. After filtering the solution, the Ph was adjusted to 4–5 and a precipitate was formed. The precipitate was collected, washed, and dried. The solid melted sharply in the range 255–257.5° C. with decomposition.

Analysis — Calcd. for $C_{21}H_{15}N_3O_2$ (percent): C, 73.89; H, 4.43; N, 12.31; Found (percent): C, 73.82, 73.76; H, 4.33, 4.40; N, 12.46, 12.54.

EXAMPLE 3

FORMATION OF A POLYMER

A sample of the mixture of 3-(p-acetamidophenyl)-2phenyl-6-carboxyquinoxaline and 3-(p-acetamidophenyl)-2-phenyl-7-carboxyquinoxaline prepared in example 1 was heated in a nitrogen gas stream at 350° C. for 4 hours. A strong flexible film which was partially soluble in meta-cresol was formed.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A compound selected from the group consisting of

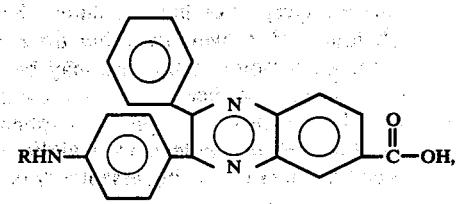

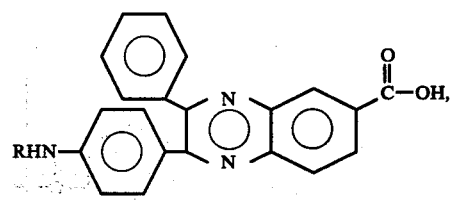

and mixtures thereof, wherein R is selected from the group consisting of

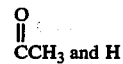

and H.

2. The compound of claim 1 wherein R is

3. The compound of claim 1 wherein R is —H.
4. A compound of the formula

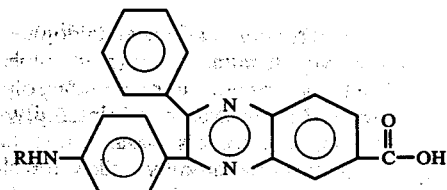

wherein R is selected from the group consisting of

—H, and mixtures thereof.

5. The compound of 4 wherein R is

6. The compound of claim 4 wherein R is —H.
7. The compound of claim 1 having the formula

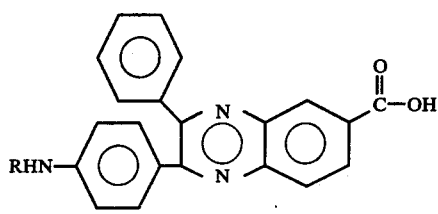

wherein R is selected from the group consisting of

—H, and mixtures thereof.

8. The compound of claim 7 wherein R is

9. The compound of claim 7 wherein R is —H.

10. A mixture of compounds of the formulas

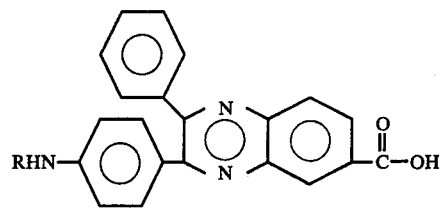

and

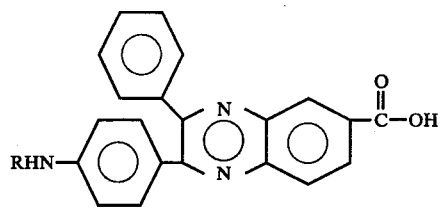

wherein R is selected from the group consisting of

and H.

11. The mixture of claim 10 wherein R is

12. The mixture of claim 10 wherein R is —H.

13. A mixture of 3-(p-acetamidophenyl)-2-phenyl-6-carboxyquinoxaline, 3-(p-acetamidophenyl)-2-phenyl-7-carboxyquinoxaline, 3-(p-aminophenyl)-2-phenyl-6-carboxyquinoxaline, and 3-(p-aminophenyl)-2-phenyl-7-carboxyquinoxaline.

* * * * *